US007538083B2

(12) United States Patent
Zurbriggen

(10) Patent No.: US 7,538,083 B2
(45) Date of Patent: May 26, 2009

(54) COMPOSITIONS AND METHODS FOR THE POTENTIATION OF IMMUNE RESPONSES AGAINST TARGET ANTIGENS

(75) Inventor: Rinaldo E. Zurbriggen, Schmitten (CH)

(73) Assignee: Intercell AG (AT)

( * ) Notice: Subject to any disclaimer, the term of this patent is extended or adjusted under 35 U.S.C. 154(b) by 461 days.

(21) Appl. No.: 10/983,169

(22) Filed: Nov. 5, 2004

(65) Prior Publication Data

US 2005/0196383 A1     Sep. 8, 2005

Related U.S. Application Data

(60) Provisional application No. 60/517,502, filed on Nov. 5, 2003.

(51) Int. Cl.
| | |
|---|---|
| *A01N 37/18* | (2006.01) |
| *A01N 43/04* | (2006.01) |
| *A61K 38/00* | (2006.01) |
| *A61K 38/16* | (2006.01) |
| *A61K 31/70* | (2006.01) |
| *A61K 39/395* | (2006.01) |
| *A61K 39/38* | (2006.01) |
| *C07K 16/00* | (2006.01) |
| *C07K 17/00* | (2006.01) |
| *C07K 5/00* | (2006.01) |
| *C07K 7/00* | (2006.01) |
| *C07K 14/00* | (2006.01) |
| *C07K 2/00* | (2006.01) |

(52) U.S. Cl. .............. 514/2; 514/8; 514/44; 424/184.1; 424/193.1; 424/185.1; 424/234.1; 424/278.1; 424/204.1; 424/265.1; 530/300; 530/330; 530/326; 530/327; 530/329; 530/333

(58) Field of Classification Search ........................ None
See application file for complete search history.

(56) References Cited

U.S. PATENT DOCUMENTS

| 5,235,038 | A | * | 8/1993 | Blondelle et al. | ............ | 530/324 |
| 6,060,056 | A | * | 5/2000 | Coutts et al. | ............. | 424/184.1 |
| 6,322,996 | B1 | * | 11/2001 | Sato et al. | ................... | 435/68.1 |
| 6,372,471 | B1 | * | 4/2002 | King | .......................... | 435/198 |
| 7,138,244 | B2 | * | 11/2006 | Barstad et al. | ................ | 435/7.1 |
| 7,208,156 | B2 | * | 4/2007 | Barstad et al. | ........... | 424/184.1 |
| 7,351,855 | B2 | * | 4/2008 | Coutts et al. | ................ | 562/400 |
| 2003/0039660 | A1 | * | 2/2003 | King et al. | ............... | 424/185.1 |
| 2003/0166548 | A1 | * | 9/2003 | Peterson et al. | ............... | 514/12 |
| 2005/0196383 | A1 | * | 9/2005 | Zurbriggen | ................ | 424/93.2 |

FOREIGN PATENT DOCUMENTS

| EP | 220957 | A | * | 5/1987 |
| EP | 1938835 | | * | 7/2008 |
| WO | 95/11975 | | | 5/1995 |
| WO | WO 98/56400 | A1 | * | 12/1998 |
| WO | WO 2005/049647 | A2 | * | 6/2005 |
| WO | WO 2007/099387 | | * | 9/2007 |
| WO | WO 2008/080628 | | * | 7/2008 |

OTHER PUBLICATIONS

Zurier et al, Annals Rheumatic Diseases, 1973, 32/5:466-470 abstract only.*
Bramwell et al, J. Drug Targeting, 2003, 11/8-10:525-530 abstract only.*
Baier et al, Immunology, 2000, 201/3-4:391-405 abstract only.*
Kind et al, Allergy: European Journal of Allergy and Clinical Immunology, 1981, 36/3:155-160.*
Martin, Report (1982) No. INIS-mf-8831, pp. 139, INIS Atomindex 1984, 15/12, Abstract No. 15:038677 abstract only.*
Baier et al, Vaccine Research, 1997, 6/3:127-140 abstract only.*
Salmon et al, JBC, 2001, 276/13:10145-10152.*
King et al, Int. Arch. Allergy Immunol., 2003, 131:25-32.*
Bowdish et al, J. Endotoxin Research, 2005, 11/4:230-236.*
King et al, J. Allergy Clin. Immunol., 1998, 101:397-403.*
Schirmbeck et al, J. Immunology, 2003, 171:5198-5207.*
Shikada et al, Prostaglandins, 1996, 51:351-361.*
Hoffman et al, FEMS Immunology and Medical Microbiology, 1997, 17:225-234.*
Boeckle et al, Journal of Controlled Release, 2006, 112:240-248.*
Zhao, Z. et al., "Immunogenicity of dinitrocarboxyphenylated melittin: The Influence of C-terminal chain shortening, N-terminal substitution and prolin insertion at positions 5 and 10." Journal of Peptide Science, vol. 1, No. 2, pp. 140-148, (1995).
Engers, H. et al. "Third meeting on Novel Adjuvants Currently in or close to clinical Testing." Butterworth Scientific. Guilford, GB, Vaccine, vol. 21, No. 25-26, pp. 3503-3524, (2003).
Mackler, B. et al. "Allergenic and biological activities of melittin from honey bee venon." Clinical Allergy, vol. 2, No. 4, pp. 317-323, (1972).
Glück, Reinhard. "Adjuvant activity of immunopotentiating reconstituted influenza virosomes (IRIVs).", Butterworth Scientific. Guilford, GB, Vaccine, vol. 17, No. 13-14, pp. 1782-1787, (1999).
Krieg, Arthur M., "CpG Motifs in Bacterial DNA and Their Immune Effects", Annu. Rev. Immunol. 20:709-760 (2002).
Gurunathan et al., "DNA Vaccines: Immunology, Application, and Optimization", Annu. Rev. Immunol. 18:927-974 (2000).
Poltl-Frank, F. et al., "Use of reconstituted influenza virus virosomes as an immunopotentiating delivery system for a peptide-based vaccine.", Clin. Exp. Immunol., 117, 496, (1999).
Moreno, Alberto. et al., "CD4+ T Cell Clones Obtained from *Plasmodium falciparum* Sporozoite-Immunized Volunteers Recognize Polymorphic Sequences of the Circumsporozoite Protein.", The Journal of Immunology, 151: 489-499, (1993).
Kumar, A. et al., "Universal" 0T Helper Cell Determinants Enhance Immunogenicity of a *Plasmodium falciparum* Merozoite Surface Antigen Peptide. The Journal of Immunology, 148, 1499-1505 (1992).
Zurbriggen, Rinaldo et al., "IRIV-adjuvanted hepatitis A vaccine: in vivo absorption and biophysical characterization." Progress in Lipid Research. 39:3-18, (2000).
Skehel, John J. and Schild, G.C., "The Polypeptide Compositio of Influenza A Viruses.", Virology 44:396-408, (1971).
Solomon, Mark J. et al., "Mapping Protein-DNA Interactions in Vivo with Formaldehyde: Evidence That Histone H4 Is Retained on a Highly Transcribed Gene.", Cell 53:937-947, (1988).
Dedon et al., "Formaldehyde Cross-Linking and Immunoprecipitation Demonstrate Developmental Changes in H1 Association with Transcriptionally Active Genes.", Molecular and Cellular Biology 11:1729-1733, (1991).

* cited by examiner

*Primary Examiner*—N. M Minnifield
(74) *Attorney, Agent, or Firm*—Proskauer Rose LLP

(57) ABSTRACT

The present invention provides novel adjuvant systems for the potentiation of immune responses against antigenic targets.

17 Claims, 3 Drawing Sheets

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial
```

```
<220> FEATURE:
<223> OTHER INFORMATION: Synthetic peptide derived from Apis mellifera

<400> SEQUENCE: 1

Lys Arg Lys Arg Gln
1               5

<210> SEQ ID NO 2
<211> LENGTH: 10
<212> TYPE: PRT
<213> ORGANISM: Artificial
<220> FEATURE:
<223> OTHER INFORMATION: Synthetic peptide derived from Apis mellifera

<400> SEQUENCE: 2

Lys Arg Lys Arg Gln Lys Arg Lys Arg Gln
1               5                   10

<210> SEQ ID NO 3
<211> LENGTH: 15
<212> TYPE: PRT
<213> ORGANISM: Artificial
<220> FEATURE:
<223> OTHER INFORMATION: Synthetic peptide derived from Apis mellifera

<400> SEQUENCE: 3

Lys Arg Lys Arg Gln Lys Arg Lys Arg Gln Lys Arg Lys Arg Gln
1               5                   10                  15

<210> SEQ ID NO 4
<211> LENGTH: 9
<212> TYPE: PRT
<213> ORGANISM: Homo Sapiens

<400> SEQUENCE: 4

Val Val Tyr Asp Phe Leu Lys Cys Met
1               5

<210> SEQ ID NO 5
<211> LENGTH: 14
<212> TYPE: PRT
<213> ORGANISM: Homo Sapiens

<400> SEQUENCE: 5

Val Val Tyr Asp Phe Leu Lys Cys Met Val Tyr Asn Ile Pro
1               5                   10

<210> SEQ ID NO 6
<211> LENGTH: 21
<212> TYPE: DNA
<213> ORGANISM: Artificial
<220> FEATURE:
<223> OTHER INFORMATION: ODN-1826

<400> SEQUENCE: 6
tccatgacgt tcctgacgt t                                              21

<210> SEQ ID NO 7
<211> LENGTH: 20
<212> TYPE: DNA
<213> ORGANISM: Artificial
<220> FEATURE:
<223> OTHER INFORMATION: ODN-1982

<400> SEQUENCE: 7
tccaggactt ctctcaggtt                                               20
```

```
<210> SEQ ID NO 8
<211> LENGTH: 8
<212> TYPE: PRT
<213> ORGANISM: Artificial
<220> FEATURE:
<223> OTHER INFORMATION: Ova 257-64

<400> SEQUENCE: 8

Ser Ile Ile Asn Phe Glu Lys Leu
1               5

<210> SEQ ID NO 9
<211> LENGTH: 9
<212> TYPE: PRT
<213> ORGANISM: Artificial
<220> FEATURE:
<223> OTHER INFORMATION: Cys-Ova 257-64

<400> SEQUENCE: 9

Cys Ser Ile Ile Asn Phe Glu Lys Leu
1               5

<210> SEQ ID NO 10
<211> LENGTH: 19
<212> TYPE: PRT
<213> ORGANISM: Artificial
<220> FEATURE:
<223> OTHER INFORMATION: Cys-Mel-Ova 257-64

<400> SEQUENCE: 10

Cys Lys Arg Lys Arg Gln Lys Arg Lys Arg Gln Ser Ile Ile Asn Phe
1               5                   10                  15

Glu Lys Leu

<210> SEQ ID NO 11
<211> LENGTH: 11
<212> TYPE: PRT
<213> ORGANISM: Artificial
<220> FEATURE:
<223> OTHER INFORMATION: Cys-Mel

<400> SEQUENCE: 11

Cys Lys Arg Lys Arg Gln Lys Arg Lys Arg Gln
1               5                   10

<210> SEQ ID NO 12
<211> LENGTH: 26
<212> TYPE: PRT
<213> ORGANISM: Apis Mellifera

<400> SEQUENCE: 12

Gly Ile Gly Ala Val Leu Lys Val Leu Thr Thr Gly Leu Pro Ala Leu
1               5                   10                  15

Ile Ser Trp Ile Lys Arg Lys Arg Glu Glu
                20                  25
```

COMPOSITIONS AND METHODS FOR THE POTENTIATION OF IMMUNE RESPONSES AGAINST TARGET ANTIGENS

CROSS-REFERENCE TO RELATED APPLICATION

This application claims the benefit of U.S. provisional patent application No. 60/517,502 filed Nov. 5, 2003, which disclosure is incorporated herein by reference.

FIELD OF THE INVENTION

The invention relates to the fields of immunology and vaccinology. Specifically, the invention relates to novel adjuvant systems that generate efficient immune responses against antigens of choice.

BACKGROUND OF THE INVENTION

Various publications or patents are referred to in parentheses throughout this application to describe the state of the art to which the invention pertains. Each of these publications or patents is incorporated by reference herein.

The last decade has seen great progress in therapeutic approaches based on vaccination against antigens present on tumor cells and infectious pathogens. Despite the advances made in the identification of new antigens and the elucidation of mechanisms that allow for targeted immune responses against such antigens, a number of challenges remain to be resolved. One obstacle, in particular, is the generation of sufficiently potent immune responses even after the identification of new antigens, as many promising antigenic targets have been shown to be only weakly immunogenic. Because such weak immune responses offer little clinical benefit, the development of effective adjuvants to enhance the immunogenicity of target antigens has become a goal of increasing therapeutic importance.

Immunization strategies to efficiently prime CD8+ T cell responses have come into focus of research activity in current vaccinology. Recent advances in the development of potent adjuvants resulted in two main, alternative approaches, i.e. peptide- and DNA-based vaccine formulation.

In genetic (nucleic acid, RNA or DNA) vaccination, the "vaccine" delivered is a plasmid DNA containing antigen-encoding sequences under control of heterologous promoters that lead to antigen expression in vivo and its immunogenic presentation. The potency to specifically prime TH1-biased immunity makes genetic vaccination an attractive candidate for prophylactic or therapeutic immunization against intracellular pathogens and cancer.

DNA-based vaccines contain unmethylated CpG motifs that stimulate innate host defense mechanisms by triggering the production of TH1-like proinflammatory cytokines, interferones and chemokines (Gurunathan et al., 2000, Annu. Rev. Immunol. 18:927-974). Similarly, synthetic oligonucleotides (ODN) with CpG motifs are potent adjuvants that facilitate priming of a specific TH1 immune responses against a wide variety of pathogens (Krieg, 2002, Annu. Rev. Immunol. 20:709-760). Thus, CpG containing ODN are attractive adjuvants for the formulation of vaccines that exploit the key cell response of the innate or specific immune system. They were shown to be effective in the specific immunotherapy of cancer and allergy in preclinical models. ODN-facilitated priming has been shown to be superior concerning magnitude and longevity of the CD8+ T cell immunity to many alternative adjuvants. In spite of many techniques to deliver ODNs, including injection of "naked", liposome-entrapped and polymer-absorbed DNA or RNA, the optimal delivery form of ODN as an adjuvant has not been elucidated yet. However, despite their promise as powerful adjuvants, the administration of both polycationic peptides and CpG containing oligonucleotides can exert toxic effects on the host, which limits their usefulness in the clinical context. It would thus be desirable to develop adjuvant systems that provide potent immune stimulation while reducing or eliminating the risk of toxic side effects.

SUMMARY OF THE INVENTION

The present invention provides novel adjuvant systems that reduce the risk of toxic side effects associated with the use of known adjuvants while providing powerful stimulation of immune responses against target antigens. These novel adjuvant systems are based on the honey bee venom melittin (SEQ ID NO: 12), or specific cationic peptides derived therefrom, and are capable of eliciting strong immune responses against target antigens. To further enhance their immunogenicity they can be optionally combined with synthetic oligonucleotides (ODNs) lacking any immunostimulatory sequences such as CpG motifs.

Thus, in one embodiment, the present invention is directed to an immunostimulatory peptide comprising SEQ ID NO: 1 and variants thereof. In another embodiment of the invention, provided are immunostimulatory peptides comprising SEQ ID NO: 12, or at least one repeat of SEQ ID NO: 1, and variants thereof.

The inventors of the present invention discovered that ODNs containing no immune-stimulatory sequences can be used to potentiate immune responses to antigens when combined with melittin-derived peptides. Thus, the present invention eliminates the risks of toxicity associated with CpG-ODNs and provides for new and safer therapeutic approaches.

In another embodiment, the present invention is directed to an immunostimulatory composition comprising an immunostimulatory peptide comprising at least one repeat of SEQ ID NO: 1 and variants thereof and further comprising at least one oligonucleotide. In a preferred embodiment at least one oligonucleotide is a non-CpG oligonucleotide. In a more preferred embodiment, the at least one oligonucleotide is complexed with the immunostimulatory peptide or covalently linked to the immunostimulatory peptide, a target antigen, or a fusion thereof.

The elimination of the requirement for immunogenic sequences in the oligonucleotides used represents a distinct advantage of the adjuvant system of the present invention, as it allows the use of non-toxic DNA and RNA sequences to stimulate immune reactions against specific antigens, without the risk of systemic immunogenicity and toxicity to the patient.

To target the immune stimulatory effect of melittin or the melittin-derived peptides optionally complexed with ODNs to specific antigenic targets, the amino acid sequence of an antigen of interest can be added to the melittin or melittin-derived peptide/ODN mixture and administered to the subject. Said target antigens may include, but are not limited to, peptides, proteins, carbohydrates, small molecules and nucleic acids, which may represent B- and T-cell antigens. One specific example for an antigen successfully used in the examples is the malaria antigen UK39.

Therefore, the present invention also comprises an immunostimulatory composition comprising melittin or melittin-derived peptides and the optional ODNs and further comprising a target antigen.

Also embraced by the present invention are fusion proteins comprising all or part of the melittin amino acid sequence fused to a target antigen. In one embodiment of the present invention the immunostimulatory peptide and the target antigen are linked by chemical conjugation. In another embodiment the immunostimulatory peptide and the target antigen are linked by a peptide bond. When fused, the peptide and antigen may be separated by spacer amino acids or spacer groups.

To further potentiate the immune stimulatory effect of melittin or the melittin-derived peptides of the present invention, the compositions comprising melittin or melittin-derived, immunostimulatory peptides, target antigens, and optionally ODNs, can further comprise a delivery vehicle. The delivery vehicle is selected from the group consisting of liposomes, virus-like particles, and virosomes.

In a preferred embodiment at least one of the immunostimulatory peptides, oligonucleotide, target antigen peptides or any fusion thereof is coupled to the surface of delivery vehicles. Alternatively, at least one of the immunostimulatory peptides, oligonucleotide, target antigen peptides or any fusion thereof is encapsulated in the delivery vehicle.

Also part of the invention is a composition, wherein at least one of the immunostimulatory peptides, oligonucleotide, target antigen peptides or any fusion thereof is encapsulated by the delivery vehicles and wherein at least one of the immunostimulatory peptides, oligonucleotide, target antigen peptides or any fusion thereof is linked to the surface of the delivery vehicles.

A preferred embodiment of the present invention, suitable to trigger the cytotoxic immune response by activation of CD8+ cells, is a immunogenic composition comprising melittin or a melittin-derived peptide along with an oligonucleotide and a target antigen encapsulated in a virosome.

To elicit the humoral immune response, the preferred composition comprises melittin or a melittin-derived peptide and a target antigen coupled to the surface of a virosome.

A method for potentiating or eliciting an immune response comprising the step of administering to a subject one of the compositions described above is also part of the present invention.

Further comprised in the present invention is the use of an immunostimulatory peptide comprising SEQ ID NO: 12, or at least one repeat of SEQ ID NO: 1, and variants thereof, for the preparation of a pharmaceutical composition for stimulating or eliciting the immune response against an antigen. In one embodiment said pharmaceutical composition for stimulating the immune response additionally comprises at least one oligonucleotide. In a preferred embodiment the at least one oligonucleotide is a non-CpG oligonucleotide. In a highly preferred embodiment said pharmaceutical composition for stimulating the immune response additionally comprises said antigen.

BRIEF DESCRIPTION OF THE DRAWINGS

FIG. 1 discloses SEQ ID NOS 9, 9, 10, 10, 10, 10, respectively, in order of appearance.

DETAILED DESCRIPTION OF THE INVENTION

Figure 1:
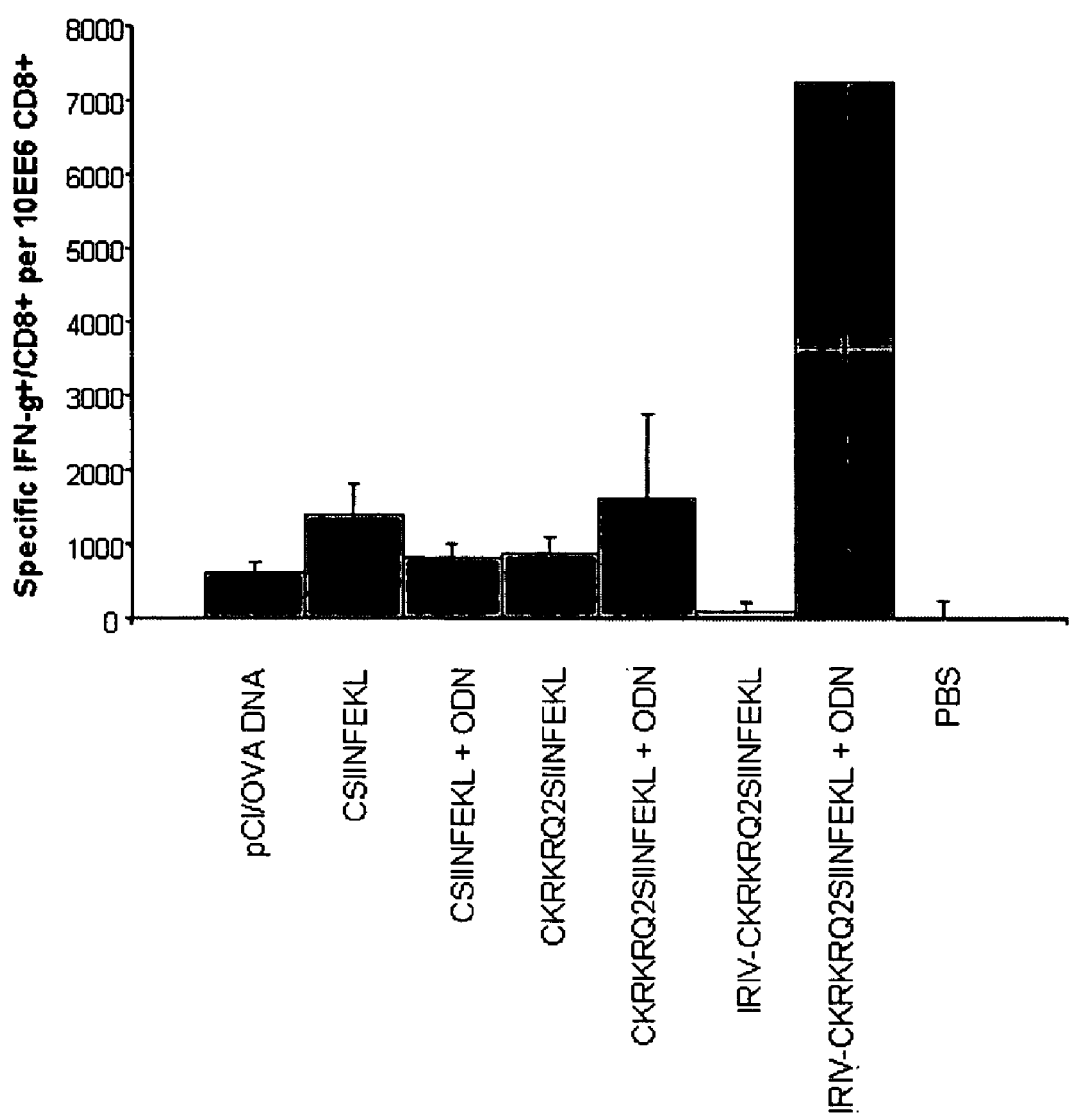
FIG. 1: This figure shows that the adjuvant effect of the melittin-derived feptide combined with antigen and oligodeoxynucleotide lacking CpG or any other immune-stimulatory motifs further synergizes with IRIVs as delivery vehicles. C57B1/6 mice were injected i.m. with 100 µl PBS containing: 100 µg pCI/OVA, 50 µg Cys-OVA257-64, 50 µg Cys-OVA257-64 +30 µg ODN-1982, 50 µg Cys-Mel-OVA257-64 +30 µg ODN-1982, virosomes with 50 µg Cys-Mel-OVA257-64 crosslinked to surface, virosomes with 50 µg Cys-Mel-OVA257-64 crosslinked to surface +30 µg ODN-1982, and control mice with PBS only. Spleen cells obtained from immunized mice 12 days after vaccination were restimulated in vitro with the OVA257-64 peptide. Mean numbers of peptide specific IFN$\gamma^+$ CD8$^+$ T cells/$10^6$ T cells±SD are shown (3 mice per group).
Figure 2:
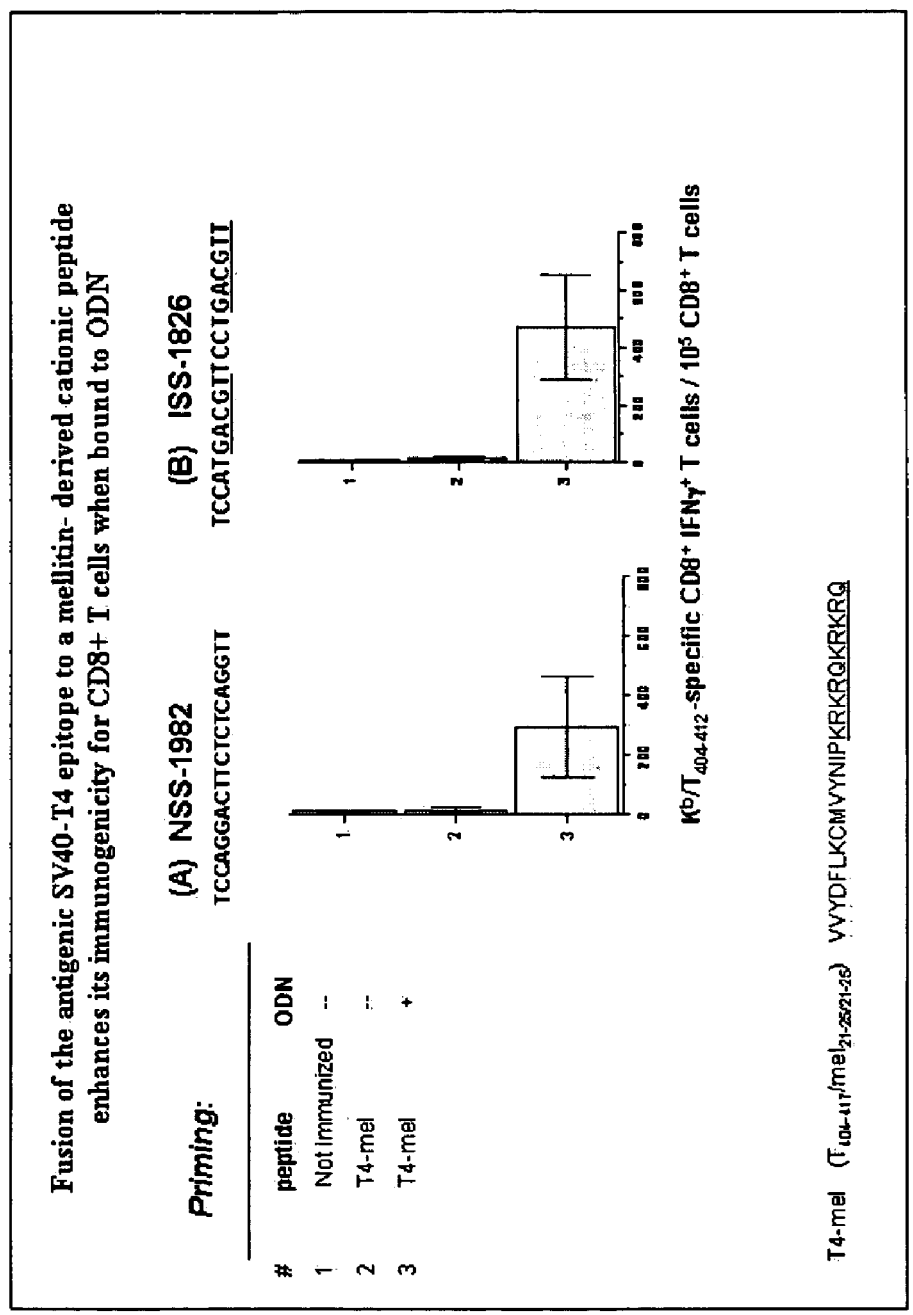
FIG. 2: This figure shows that a melittin-derived peptide (KRKRQKRKRQ; SEQ ID NO: 2) shows significant adjuvant activity when combined with a target antigen (T4) and an oligodeoxynucleotide. Remarkably, the adjuvant activity of the melittin-derived peptide does not depend on the presence of CpG motifs in the oligodeoxynucleotide. The adjuvant activity of the melittin-derived peptide thus acts synergistically even with oligodeoxynucleotides that lack any immunostimulatory sequences. C57BL/6 (B6) mice were either not immunized (group 1) or vaccinated i.m. with 35 nmol of peptides alone (group 2) or mixed with oligodeoxynucleotide (group 3), not containing (A; NSS$^+$ ODN-1982; SEQ ID NO: 7), or containing (B; ISS$^+$ ODN-1826; SEQ ID NO: 6) CpG motifs. Spleen cells obtained from immune mice 12 days post vaccination were restimulated ex vivo with the T4 peptide VVYDFLKCM ($K^b/T_{404-412}$, SEQ ID NO: 4). Mean number of specific IFN$\gamma^+$ CD8$^+$ T cells/$10^5$ CD8$^+$ T cells±SD (of 6 mice per group) averaged from two independent experiments are shown.
Figure 3:
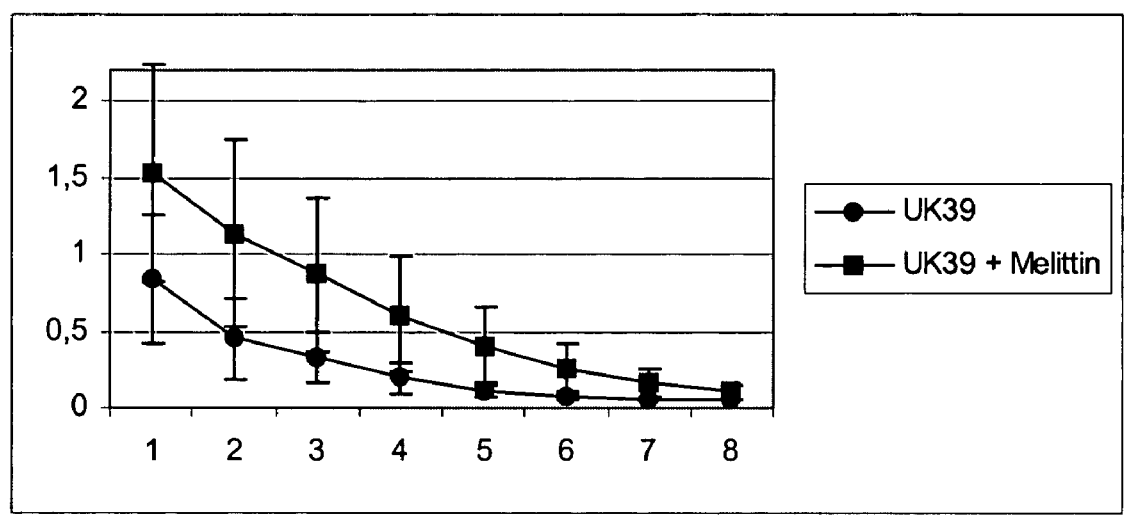
FIG. 3 demonstrates that the humoral immune response (B cell immunity) against an antigen coupled to the surface of a IRIV can be further enhanced by the addition of melittin (SEQ ID NO: 12). Balb/c mice were immunized with 100 µl PBS containing: the malaria mimetic UK39 (20 µg UK39) in combination with an IRIV with or without 10 µg Melittin. For the UK39 ELISA, ELISA plates were coated over night at 4° C. with 10 µg/ml UK39 in PBS. After washing with PBS 0.05% Tween20 plates were blocked with 5% dry milk in PBS 2 h at 37° C. Mouse sera from day 21 and 35 were initially diluted 1:10 and titrated in serial 1:2 dilutions in PBS 0.05% Tween20 0.5% dry milk. After 2 h incubation at 37° C. plates were washed and incubated with goat □-mouse IgG HRP Ab (BD Bioscience) (1:5000 in PBS 0.05% Tween20 0.5% dry milk) 1 h 37° C. Plates were developed with OPD-substrate (OPD (O-Phenylenediamine tablets, Fluka, Switzerland, 1 tablet in 50 ml citrate buffer+50 µl H2O2) for 30 min. The reaction was stopped with 1 M H2SO4 and plates were read at 492 nm.

The present invention provides novel adjuvant systems based on a set of novel peptides derived from the honey bee venom protein melittin, that reduce the risk of toxic side effects associated with the use of known adjuvants while providing powerful stimulation of immune responses against target antigens. In particular, the present invention provides novel peptides capable of eliciting strong immune responses against target antigens when combined with oligonucleotides (ODNs) lacking any immunostimulatory sequences such as CpG motifs.

Immunostimulatory ODNs have previously been used as DNA vaccines, it was heretofore believed that their immunogenicity correlated with their sequences, for example comprising unmethylated CpG motifs, that are recognized by the host immune system as foreign or of bacterial origin, thereby triggering an immune response. The same sequences within the ODNs responsible for this adjuvant effect, however, are known to be toxic to the host. For example, it has been shown that, at relatively low doses of administration, ODNs containing immunostimulatory motifs can induce inflammatory reactions and lead to septic shock in the host, neither of which would be an acceptable side effect in clinical applications.

The present invention's unexpected finding that ODNs containing no immune-stimulatory sequences can be used to potentiate immune responses to antigens when combined with melittin-derived peptides eliminates the risks of toxicity associated with CpG-ODNs and provides for new and safer therapeutic approaches. Thus, the discovery that the synergistic immune stimulatory effect of melittin-derived peptides is not dependent on the presence of CpG sequences in oligonucleotides that complex to the peptides is of great import.

The present invention shows that fusing a sample antigen to a melittin-derived peptide and binding oligonucleotides to them creates potent immunogens for $CD8^+$ T (killer T) cells and that oligonucleotides lacking any immunogenic sequences can interact synergistically with melittin-derived peptides to create a potent adjuvant effect against a target antigen of choice.

The elimination of the requirement for immunogenic sequences in the oligonucleotides used represents a distinct advantage of the adjuvant system of the present invention, as it allows the use of non-toxic nucleic acid sequences to stimulate immune reactions against specific antigens, without the risk of systemic immunogenicity and toxicity to the patient.

In addition, the peptides derived from melittin and melittin itself represent potent immunogens for eliciting the humoral immune response (B-cell response) against a target antigen, optionally coupled to the surface of a virosome. Herein, the melittin or melittin-derived peptide can also be directly fused to the antigen. In contrast to the cytotoxic T-cell immunity, the humoral antibody-based B-cell immunity might possibly not be further enhanced by the addition of immunostimulatory oligonucleotides.

Thus, the present invention provides immune-stimulatory compositions comprising melittin (SEQ ID NO: 12), as well as melittin-derived peptides including, but not limited to, the sequence KRKRQ (SEQ ID NO: 1) and multiples thereof, and optionally further comprising oligonucleotides that require no immunogenic sequence, motif or modification in order to synergistically potentiate the immunostimulatory effect of the melittin-derived peptides.

In a preferred embodiment, the compositions of the present invention elicit the cytotoxic immunity, based on CD8+ cells, by comprising melittin or a melittin-derived immunogenic peptide, a target antigen encapsulated in a carrier vehicle, preferably a virosome, and an oligonucleotide, preferably a non-CpG oligonucleotide.

In another preferred embodiment the compositions of the present invention serve to trigger the antibody-based B-cell immunity and, thus, comprise melittin or a melittin-derived immunogenic peptide and an antigen of choice coupled to the surface of a carrier vehicle, preferably a virosome.

The oligonucleotides are thought to bind to the melittin-derived peptides via electrostatic interactions between the negatively charged phosphate backbone of the nucleic acids with the positively charged amino acids present in the peptides. Therefore, no chemical manipulations other than simple co-incubation are required to complex the peptides with the ODNs.

To target the immune stimulatory effect of the melittin-derived peptides optionally complexed with ODNs to specific antigenic targets, the amino acid sequence of an antigen of interest can be added to the melittin or melittin-derived peptide/ODN mixture and administered to the subject. Said antigens comprise, but are not limited to, peptides, proteins, carbohydrates, small molecules and nucleic acids, which represent B- and T-cell antigens. One example for a target antigen, which was successfully tested under experimental conditions, is the malaria mimetic UK 39.

Instead of relying on the electrostatic interactions between the melittin-derived peptides of the instant invention and ODNs, the peptides and oligonucleotides can be covalently linked to yield peptide-oligonucleotide fusion molecules, comprising at least one ODN coupled to the melittin-derived peptide, the target antigen or a fusion of both.

To further potentiate the immune stimulatory effect of the melittin-derived peptides of the present invention, the compositions comprising melittin or melittin-derived peptides, target antigens, and ODNs, can be coupled to the surface of delivery vehicles, such as virosomes, by the methods disclosed herein. Alternatively, the melittin or melittin-derived peptides, ODNs and target antigen peptides may be encapsulated in delivery vehicles by methods disclosed herein. As an alternative, the melittin or melittin-derived peptides, ODNs and target antigens can be both encapsulated by and linked to the surface of the delivery vehicles.

It should be noted that based on the instant disclosure, a person of skill in the art would be motivated and able to perform a variety of permutations to the delivery vehicle formulations of the present invention, including the linking of various combinations of melittin or melittin-derived peptides, ODNs, and/or target antigen to the surface of the delivery vehicle, and the same or different combinations encapsulated within the delivery vehicles. It will be understood that many variations can be made in the combinations described, while still remaining within the bounds of the invention. It is the intention of the inventors that such variations are included within the scope of the invention.

Melittin and the melittin-derived peptides of the present invention may be produced by chemical synthesis, or they may be of natural or recombinant origin. Melittin or melittin-derived peptides may be recombinantly produced using a nucleic acid molecule encoding the peptide(s). In addition, their sequences may be modified sequence as long as they retain the ability to stimulate the immune responses to antigens disclosed herein.

Thus, in a further preferred embodiment, the invention embraces functional variants of melittin-derived peptides. As used herein, a "functional variant" or "variant" of a melittin-derived peptide is a peptide which contains one or more modifications to the primary amino acid sequence of an immunostimulatory melittin-derived peptide while retaining the immunostimulatory effect disclosed herein. If a functional variant of a melittin-derived peptide involves an amino acid substitution, conservative amino acid substitutions typically will be preferred, i.e., substitutions which retain a property of the original amino acid such as charge, hydrophobicity, conformation, etc. Examples of conservative substitutions of amino acids include substitutions made among amino acids within the following groups: (1) M, I, L, V; (2) F, Y, W; (3) K, R, H; (4) A, G; (5) S, T; (6) Q, N; and (7) E, D.

Modifications which generate functional variants of melittin-derived peptides may be made in order to enhance peptide stability in an expression system, to enhance the stability of protein-protein binding such as HLA-peptide binding, or to increase the avidity of immune receptors. Again, any method for preparing modified or variant peptides can be employed, such as synthesis of the modified or variant peptide or its recombinant production using a mutated nucleic acid molecule.

The identification of additional or optimized immunostimulatory melittin-derived peptides may also include the step of comparing the stimulation of T or B cells by the melittin-derived peptide and the stimulation of T or B cells by the functional variant as a determination of the effectiveness of the stimulation of immune effector cells by the functional variant. By comparing the functional variant melittin-derived peptide with a known melittin-derived peptide, peptides with increased immune cell stimulatory properties can be prepared.

The individual melittin-derived peptides may also have one or more amino acids added to either or both ends. Thus, for example, linker or spacer amino acids may be added to the N- or C-terminus of the peptides or both, to allow for convenient coupling of the peptides to a delivery vehicle such as a virosome.

The present invention also embraces fusion proteins comprising all or part of a melittin-derived peptide amino acid sequence fused to a target antigen or the linkage of both by chemical conjugation (covalently bonded directly via side chain bonds or via a linker or spacer group). When fused, the melittin-derived peptide and antigen may be separated by spacer amino acids. In a preferred embodiment, the melittin-derived peptides are constructed from the sequential arrangement of melittin-derived peptide amino acid sequences. Thus, a fusion peptide can contain multimers of the melittin-derived peptide sequence, or variants thereof, linked to an antigenic peptide sequence of choice. Such multiepitope peptides can include universal T helper peptide amino sequences, in flanking, nested, or overlapping arrangements. Universal T helper epitopes are well known in the art and may be derived from HBV core and surface antigens, tetanus toxoid, *pseudomonas aeruginosa* toxin A, beta-galactosidase, *brucella abortus*, keyhole limpet hemocyanin, influenza virus hemagglutinin and nucleoprotein, malaria circumsporozoite, ovalbumin, and others known by persons skilled in the art.

The present invention also demonstrates that the combination of virosomes (IRIVs) as human compatible immunopotentiating delivery agents with the compositions of the present invention further potentiates the generation of efficient immune responses against target antigens. Thus, the invention provides novel peptide adjuvants the immunogenic efficacy of which can be further enhanced by their combination with an immunopotentiating delivery system. While immunopotentiating reconstituted influenza virosomes (IRIVs) are well suited, a number of other delivery vehicles, such as liposomes, virus-like particles, multiple-antigen peptides (MAPs) and the like are also available to a person of skill in the art. IRIVs consist of spherical, unilammelar virus-like particles prepared from a mixture of phospholipids and influenza virus surface glycoproteins, but they do not contain any viral nucleic acids. The hemagglutinin membrane glycoprotein of the influenza virus plays a key role in the mode of action of IRIVs. This major antigen of the influenza virus is a membrane fusion-inducing component, which facilitates antigen delivery to immunocompetent cells. IRIVs are known to act as efficient and highly effective means of enhancing the immune response with an excellent safety profile.

The IRIV delivery system of the invention further potentiates the immune response elicited by the compositions of the present invention against target antigens. Like liposomes, virosomes can be used to deliver therapeutic substances to a wide variety of cells and tissues, but unlike liposomes, virosomes offer the advantage of efficient entry into the cells followed by the intracellular release of the virosomal contents triggered by the viral fusion protein. Moreover, due the incorporation of active viral fusion proteins into their membranes, virosomes release their contents into the cytoplasm immediately after being taken up by the cell, thereby preventing the degradation of the therapeutic substance in the acidic environment of the endosome. IRIVs can further be loaded simultaneously with several different B-cell and T-cell epitopes (Poltl-Frank, F. et al., *Clin. Exp. Immunol.,* 1999, 117, 496; Moreno, A. P. et al., J. Immunol., 1993, 151: 489) including universal T-helper cell epitopes (Kumar, A. et al., J. Immunol. 1992, 148, 1499-1505) and others known to those of skill in the art.

As evidenced by the results shown herein, IRIVs have great potential in the design of combined vaccine/adjuvant systems. Furthermore, IRIV-based peptide vaccines would be expected to be safe, since IRIV-based protein vaccines have already shown a very good safety profile in humans (Glueck, R., Vaccine 1999, 17, 1782). The concerted action of the peptide adjuvant of the present invention combined with ODNs and an antigenic target, together with the use of IRIVs as an efficient human-compatible delivery system, represents a significant advance in the design of prophylactic as well as therapeutic vaccines against a wide variety of diseases.

The present invention also provides for the administration of the immunostimulatory compositions, such as the melittin-derived peptides and antigens in combination with ODNs and virosomes or equivalent delivery vehicles in a suitable pharmaceutical formulation. By administration or administering is meant providing one or more peptides or peptide-containing compositions of the invention as a drug, prodrug, or a drug-metabolite, to an individual in need thereof. Such a drug which contains one or more of the melittin-derived peptides and/or peptide containing compositions of the present invention, as the principal or member active ingredient, can be administered in a wide variety of therapeutic dosage forms in the conventional vehicles for topical, oral, systemic, local, and parenteral administration. Thus, the invention provides compositions for parenteral administration which comprise a solution of the melittin-derived peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others. Thus, a typical pharmaceutical composition for intradermal infusion could be made up to contain 250 ml of sterile Ringer's solution, and 100 mg of peptide. Actual methods for preparing parenterally administrable compounds will be known or apparent to those skilled in the art and are described in more detail in for example, Remington: The Science and Practice of Pharmacy ("Remington's Pharmaceutical Sciences") Gennaro A R ed. 20th edition, 2000: Williams & Wilkins PA, USA, which is incorporated herein by reference.

The route and regimen of administration will vary depending upon the stage or severity of the condition to be treated, and is to be determined by the skilled practitioner. For example, the peptides and peptide-containing compositions can be administered in such oral dosage forms for example as tablets, capsules (each including timed release and sustained release formulations), pills, powders, granules, elixirs, tinctures, solutions, suspensions, syrups and emulsions, or by injection. Similarly, they may also be administered in intravenous (either by bolus or infusion methods), intraperitoneal, subcutaneous, topical with or without occlusion, or intramuscular form. In preferred embodiments, the peptides and peptide-containing compositions are administered intradermally or subcutaneously. All of these forms are well known to those of ordinary skill in the pharmaceutical arts.

The daily dose of the melittin-derived peptides and compositions of the invention may be varied over a range from 0.001 to 1,000 mg per adult per day. For oral administration, the compositions are preferably provided in the form of tables containing from 0.001 to 1,000 mg, preferably 0.001, 0.01, 0.05, 0.1, 0.5, 1.0, 2.5, 10.0, 20.0, 50.0, 100.0 milligrams of active ingredient for the symptomatic adjustment of dosage according to signs and symptoms of the patient in the course of treatment. An effective amount of drug is ordinarily supplied at a dosage level of from about 0.0001 mg/kg to about 50 mg/kg of body weight per day. The range is more particular from about 0.0001 mg/kg to 7 mg/kg of body weight per day.

Advantageously, suitable formulations of the present invention may be administered in a single daily dose, or the total daily dosage may be administered in divided doses for example of two, three, or four times daily. Furthermore, compounds of the present invention, particularly those containing virosomes or liposomes, can be administered in intranasal form, or via transdermal routes known to those of ordinary skill in the art. To be administered in the form of a transdermal delivery system, the dosage administration will, or course, be continuous rather than intermittent throughout the dosage regimen.

The melittin-derived peptides and compositions of the present invention may be administered in a pharmaceutical composition comprising the active compound in combination with a pharmaceutically acceptable carrier adapted for topical administration. Topical pharmaceutical compositions may be, for example, in the form of a solution, cream, ointment, gel, lotion, shampoo, or aerosol formulation adapted for application to the skin. These topical pharmaceutical composition containing the compounds of the present invention ordinarily include about 0.005% to 5% by weight of the active compound in admixture with a pharmaceutically acceptable vehicle.

The dosage regimen utilizing the compositions of the present invention is selected in accordance with a variety of factors, including for example species, age, weight, sex and medical condition of the patient, the stage and severity of the condition to be treated, and the particular compound thereof employed. A physician of ordinary skill can readily determine and prescribe the effective amount of the drug required to prevent, counter, or arrest the progress of a malignancy or infectious disease. Optimal precision in achieving concentration of drug with the range that yields efficacy either without toxicity or with acceptable toxicity requires a regimen based on the kinetics of the drug's availability to target sites. This process involves a consideration of the distribution, equilibrium, and elimination of the drug, and is within the ability of the skilled practitioner.

In the methods of the present invention, the compounds herein described in detail can form the active ingredient and are typically administered in admixture with suitable pharmaceutical diluents or excipients suitably selected with respect to the intended form of administration, that is, oral tablets, capsules, elixirs, syrups, and the like, and consistent with conventional pharmaceutical practices. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, aga, bentonite, xanthan gum and the like.

The liquid forms may be suitably flavored suspending or dispersing agents such as the synthetic and natural gums, for example, tragacanth, acacia, methyl cellulose and the like. Other dispersing agents which may be employed are glycerin and the like. For parenteral administration, sterile suspensions and solutions are desired. Isotonic preparations which generally contain suitable preservatives are employed when intravenous administration is desired. Topical preparations containing the active drug component can be admixed with a variety of carrier materials well known in the art, such as, for example, alcohols, aloe vera gel, allatoin, glycerine, vitamins A or E oils, mineral oil, PPG2 myristyl propionate, and the like, to form, for example, alcoholic solutions, topical cleansers, cleansing creams, skin gels, skin lotions, and shampoos in cream or gel formulations.

The melittin-derived peptides, compositions, or formulation thereof of the present invention may be coupled to a class of biodegradable polymers useful in achieving controlled release of a drug, for example, polylactic acid, polyepsilon caprolactone, polyhydroxy butyric acid, polyorthoesters, polyacetals, polydihyrdo-pyrans, polycyanoacrylates, and cross-linked or amphipathic block copolymers of hydrogels. Generally, subjects can receive an intradermal injection of an effective amount of the melittin-derived peptides and compositions either in combination with delivery vectors, such as virosomes, or by themselves. The peptides of the present invention can also be administered in the form of liposome delivery systems, such as small unilamellar vesicles, large unilameller vesicles and multilamellar vesicles. Liposomes can be formed from a variety of compounds, including for example cholesterol, stearylamine, and various phosphatidylcholines.

Initial doses can be followed by booster doses, following immunization protocols standard in the art. The immunostimulatory effect of the compositions and methods of the instant invention can be further increased by combining any of the above-mentioned melittin-derived peptide compositions, including their combination with virosomes, with an immune response potentiating compound. Immune response potentiating compounds are classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include Freund's, alum, mycobacteria such as BCG and *M. Vaccae*, quil-saponin mixtures such as QS-21 (SmithKline Beecham), and various oil/water emulsions (e.g. IDEC-AF). Cytokines are also useful in vaccination protocols as a result of lymphocyte stimulatory properties. Many cytokines useful for such purposes will be known to one of ordinary skill in the art, including interleukin-2 (IL-2), IL-12, GM-CSF and many others.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The preparations of the invention are administered in effective amounts. An effective amount is that amount of a pharmaceutical preparation that alone, or together with further doses, stimulates the desired response. Generally, doses of immunogens ranging from one nanogram/kilogram to 100 miligrams/kilogram, depending upon the mode of administration, are considered effective. The preferred range is believed to be between 500 nanograms and 500 micrograms per kilogram. The absolute amount will depend upon a variety of factors, including the composition selected for administration, whether the administration is in single or multiple doses, and individual patient parameters including age, physical condition, size, weight, and the stage of the disease. These factors are well known to those of ordinary skill in the art and can be addressed with no more than routine experimentation.

In the case of treating cancer, the desired response is inhibiting the progression of the cancer and/or inducing the regression of the cancer and its metastases. In the case of treating an infectious disease, the desired response is control of the infection and/or clearance of the infectious agent from the system. In the case of prophylaxis, the desired response is protective immunity to the agent, as measured by secondary immune responses upon exposure to the agent or an antigen thereof. These desired responses can be monitored by routine methods or can be monitored according to diagnostic methods of the invention discussed herein. The present invention is not to be limited in scope by the specific embodiments described herein. Indeed, various modifications of the invention in addition to those described herein will become apparent to those skilled in the art from the foregoing description, as well as from the examples. Such modifications are intended to fall within the scope of the appended claims.

Definitions

Amino acids and amino acid residues described herein may be referred to according to the accepted one or three letter code referenced in text books well known to those of skill in the art, such as Stryer, Biochemistry, 4$^{th}$ Ed., Freeman and Co., New York, 1995 and Creighton, Proteins, 2$^{nd}$ Ed. Freeman and Co. New York, 1993.

As used herein, the terms "peptide" and "polypeptide" are used synonymously and in their broadest sense to refer to a compound of two or more amino acid residues, or amino acid analogs. The amino acid residues may be linked by peptide bonds, or alternatively by other bonds, e.g. ester, ether etc. As used herein, the term "amino acid" or "amino acid residue" refers to either natural and/or unnatural or synthetic amino acids, including both the D or L enantiomeric forms, and amino acid analogs.

By "melittin-derived peptide" is meant an amino acid sequence derived from the protein melittin and more particularly the KRKRQ (SEQ ID NO: 1) sequence from the C-terminal region of melittin, a component of the venom of the honey bee. This sequence may further be multimerized into repeats, such as a dimer KRKRQKRKRQ (SEQ ID NO: 2), or trimer KRKRQKRKRQKRKRQ (SEQ ID NO: 3), and so forth. The individual amino acids of the melittin-derived peptides may also be conservatively substituted with amino acids of equivalent size, charge and/or polarity. In addition, suitable linker amino acids may be added to either end of the melittin-derived peptides in order to facilitate their incorporation into delivery vehicles and/or their fusion to target antigens.

A "target antigen" as used herein is a peptide, protein or carbohydrates derived from a pathogen or malignant cell against which an immune response is desired. Target antigens of interest include tumor-specific and tumor-associated antigens, as well as antigens from bacterial, viral, and other infectious organisms, all of which are well known in the art.

The term "ODN" as used herein refers to all oligonucleotide molecules, including both oligodeoxyribonucleotide and oligoribonucleotide molecules. The ODNs may have phosphodiester-modified backbones to improve stability. A particular advantage of the present invention is that ODNs of any sequence can be used to elicit effective immune responses, thereby obviating the need for nonmethylated DNA, CpG motifs, or other sequences previously shown to be immunogenic which carry an inherent risk of toxicity and thus would require chemical modification prior to clinical use. The length of ODNs suitable for the purposes of the present invention can range from about 10 to about 60 nucleotides, although both shorter and longer ODNs may be suitable for the adjuvant system of the present invention.

The term "epitope" as used herein, refers to those parts of a molecule that are recognized by T cell and/or B cell receptors.

The term "antigen" is used herein to describe a molecule that binds to a T cell receptor or antibody and whose immunogenicity can be enhanced or potentiated by the adjuvants disclosed herein.

The term "adjuvant" refers to a substance distinct from target antigen that is capable of enhancing or potentiating immune effector cell activation.

The term "adjuvant systems" is used herein to denote the combination of various immune-stimulatory peptides, such as the melittin-derived peptides of the present invention, with target antigens and oligonucleotides to potentiate the immune stimulatory effect that each component of the system would exert if used by itself, as well as their combination with a suitable delivery system, such as virosomes, which may further increase the immune stimulatory effect of the compositions.

The term "potentiating" or "immunopotentiating" is used herein to refer to an adjuvant or enhancing effect on immune functions which may occur through stimulation of immune effector cells and may lead to destruction or clearance of antigen-bearing pathogens or malignancies, and/or to immunity thereto.

As used herein, a "functional variant" or "variant" of a melittin-derived peptide means a peptide which contains one or more modifications to the primary amino acid sequence of an immunostimulatory melittin-derived peptide while retaining the immunostimulatory effect disclosed herein.

By "administration" or "administering" is meant providing one or more peptides or peptide-containing compositions of the invention as a drug, pro-drug, or a drug-metabolite, to an individual in need thereof.

An "effective amount" is that amount of a pharmaceutical preparation that alone, or together with further doses, stimulates the desired response.

EXAMPLES

The following examples are provided to better illustrate the claimed invention and are not to be interpreted as limiting the scope of the invention. To the extent that specific materials are mentioned, it is merely for purposes of illustration and is not intended to limit the invention. Unless otherwise specified, biochemical and molecular biology procedures, such as those set forth in Voet, *Biochemistry*, Wiley, 1990; Stryer 1995; *Peptide Chemistry. A Practical Textbook,* 2nd ed., Miklos Bodanszky, Springer-Verlag, Berlin, 1993; Sambrook et al., Molecular Cloning, Cold Spring Harbor Laboratory (2001), Ausubel et al. (Eds.) Current Protocols in Molecular Biology, John Wiley & Sons (2000) are used. One skilled in the art may develop equivalent means or reactants without the exercise of inventive capacity and without departing from the scope of the invention. It will be understood that many variations can be made in the compositions and procedures herein described while still remaining within the bounds of the present invention. Likewise, it is understood that, due to known structural or chemical similarities such as polarity, bulk, or orientation between amino acid side chains, peptide sequences with amino acids or replacement structures equivalent to those disclosed herein will retain similar function. It is the intention of the inventors that such variations are included within the scope of the invention.

Example 1

This example shows that a melittin-derived peptide (mel, KRKRQKRKRQ, SEQ ID NO: 2) is not dependent on the presence of CpG sequences in the ODN to show its full adjuvant activity. Fusion of a sample antigen (here, T4 peptide) to the melittin-derived peptide and binding ODN to them creates potent immunogens for $CD8^+$ T cells. A sample target antigen, the SV40-derived T4 peptide T404-417 VVYD-FLKCMVYNIP (SEQ ID NO: 5) was fused to a duplicated amino acid sequence derived from melittin (KRKRQKRKRQ, SEQ ID NO: 2). B6 mice were vaccinated i.m. with 35 nmol of these peptides alone (group 2), or mixed with ODN (group 3), not containing (A; NSS+ ODN-1982), or containing (B; ISS+ ODN-1826) CpG motifs (FIG. 1). Spleen cells obtained from immune mice 12 days post-vaccination were restimulated ex vivo with the T4 peptide VVY-DFLKCM (SEQ ID NO: 4) (Kb/T404-412). Mean numbers of specific $IFN\gamma^+$ $CD8^+$ T cells/$10^5$ $CD8^+$ T cells±SD (of 6 mice per group) averaged from two independent experiments are shown.

C57BL/6JBom (B6) mice (H-2b) were bred and kept under standard pathogen-free conditions in the animal colony of Ulm University (Ulm, Germany). Male/female mice were used at 12-16 wks of age. The preparation of cationic peptide/ODN vaccines CpG containing ODN-1826 (TCCAT-GACGTTCCTGACGTT; ISS-1826, SEQ ID NO: 6) and its control ODN-1982 (TCCAGGACTTCTCTCAGGTT; NSS-1982, SEQ ID NO: 7) were obtained from MWG (Ebersberg, Germany). ODN were synthesized with phosphorothioate backbones. ODN were dissolved in water at a 10 mg/ml stock solution. The synthetic peptides used in the present work were obtained from Jerini BioTools (Berlin, Germany). Peptides were dissolved in water or DMSO at a concentration of 10 mg/ml. Where indicated ODN were incubated for 30 mm with peptides in PBS pH 7.4. 50 µl PBS were injected i.m. into each tibialis anterior muscle (or 100 µl s.c. into the base of the tail). For the determination of splenic $CD8^+$ T cell frequencies spleen cells ($1\times10^7$/ml) were incubated for 1 h in RPMI-1640 medium with 1 µg/ml of the indicated antigen-specific or non-specific control peptides. Thereafter, 5 µg/ml Brefeldin A (BFA) (cat.no.15870; Sigma) was added, and the cultures were incubated for another 4 h. Cells were harvested and surface stained with PE-conjugated anti-CD8 mAb (cat.no.01045B; Pharmingen). Surface stained cells were fixed with 2% (w/v) paraformaldehyde in PBS before intracellular staining for $IFN\gamma$. Fixed cells were resuspended in permeabilization buffer 8 (HBSS, 0.5% (w/v) BSA, 0.5% (w/v) saponin, 0.05% (w/v) sodium azide) and incubated with FITC-conjugated anti-$IFN\gamma$ mAb (cat.no.55441; Pharmingen) for 30 mm at RT and washed twice in permeabilization buffer. Stained cells were resuspended in PBS supplemented with 0.3% (w/v) BSA and 0.1% (w/v) sodium azide. The number of $CD8^+$ $IFN\gamma^+$ T cells per $10^5$ splenic $CD8^+$ T cells was determined by FCM analyses.

Example 2

This example shows how the immune-stimulatory compositions of the present invention, including melittin-derived peptides and target antigens, can be coupled to the surface of virosomes. Chemicals: Octaethyleneglycol-mono-(n-dodecyl)ether (OEG, C12E8) was from Fluka. Egg phosphatidyl choline (PC) was obtained from Lipoid (Cham, Switzerland). Phosphatidylethanolamine (PE) was obtained from R. Berchtold (Biochemical Laboratory, University of Bern, Switzerland). N-γ-maleimidobutyryloxysuccinimide ester (GMBS) was purchased from Pierce (cat. no. 22309). Peptides were purchased from Bachem (Bubendorf, Switzerland). Biobeads SM2 and Bio-Gel A-15m were from Bio-Rad Laboratories (Glattbrugg, Switzerland).

Peptide bearing influenza virosomes (IRIVs) were prepared by first crosslinking the Cys-terminus of the peptide to PE via GMBS. Briefly, 10 mg PE was resuspended in 200 µl chloroform/methanol 9:1 and 5 µl triethylamine (99%) before 1.7 mg GMBS was added. The mixture was incubated at RT for 1 h with gentle agitation and then concentrated on a speedvac at RT. The pellet was resuspended in 2 ml 100 mM OEG in PBS (OEG-PBS) and 6 mg Cys-Mel (CK-RKRQKRKRQ, SEQ ID NO: 11) was added. After 1 h incubation at RT it was mixed with 4 mg influenza A/Singapore and 32 mg PC resuspended in 2 ml OEG-PBS. The mixture was sonicated for 1 min and centrifuged for 1 h at 100,000×g at RT. The supernatant was sterile filtered and OEG was removed by incubation with 180 mg of wet SM2 Bio-Beads once for 1 h at RT with shaking and three times for 30 min with 90 mg of SM2 Bio-Beads.

Example 3

This example shows the preparation of IRIV with encapsulated molecules: IRIV were basically prepared as described by Zurbriggen et al. (Zurbriggen et al., Prog. Lipid Res. 39:3-18, 2000). Briefly, 32 mg egg PC and 8 mg PE were dissolved in 2 ml of PBS containing 100 mM OEG (PBS/OEG). Influenza A/Singapore was purified as described (Skehel and Schild, Virology 44:396-408, 1971). Influenza virus corresponding to 4 mg hemagluttinin (HA) was centrifuged at 100,000×g for 1 hour and the pellet was dissolved in 1 ml of PBS/OEG. To prepare antigen and/or melittin-IRIV, 4 mg of peptide was dissolved in 1 ml PBS/OEG. The phospholipids, the dissolved virus solution and the peptide and ODN solutions were mixed and sonicated for 1 min. This mixture was centrifuged at 100,000×g for 1 h and the supernatant sterile filtered (0.22 µm). Virosomes were then formed by detergent removal using 1.23 g of wet SM2 Bio-Beads for 1 h at room temperature with shaking and three times for 30 min with 0.6 g of SM2 Bio-Beads. Size determination of IRIV was done by light scattering using a Zetasizer 1000HS instrument (Malvern Instruments, UK). For quantification of encapsulated antigen and/or melittin, a fraction of the homogenous IRIV were loaded on a Sephadex G50 Coarse (Amersham Biosciences, Switzerland) gel-filtration column and separated from non-encapsulated peptide. Peptide quantification was done on an Äkta Explorer 10 (Amersham Biosciences, Switzerland) using a CC 125/4.6 Nucleosil 100-5 C8 reverse-phase column (Macherey-Nagel, Switzerland).

Example 4

This example shows an alternative method of encapsulating molecules in IRIVs. Chemicals: 1,2-Dipalmitoyl-sn-gylcero-3-phospho-rac-(1-glycerol) (PG) were purchased from Sigma (Buchs, Switzerland).

Preparation of large unilamellar vesicles (LUVs): 36.4 µmol (27.95 mg) PC and 15.6 µmol (10.75 mg) PG (molar ratio 70:30) were dissolved in methanol/chloroform (2:1). The solvent was removed by using a rotary evaporator (Rotavapor R-205, Büchi Labortechnik, Switzerland) at 40° C. at a gradual vacuum of 30-10 kPa. For antigen and/or melittin-liposomes with hydrophobic antigen and/or melittin, 2-3.5 mg antigen and/or melittin was dissolved in methanol and added to the phospholipid mixture before solvent removal. The dried lipid film was hydrated with 500 µl PBS. For antigen and/or melittin-liposomes with hydrophilic antigen and/or melittin, the dried lipid film was hydrated with 350 µl PBS containing 2-3.5 mg peptide to be encapsulated. Before extrusion, the volume was adjusted to 500 µl with PBS. The liposome dispersion was extruded ten times through polycarbonate membranes (Nucleopore Track-Etch membrane, 0.1 µm or 0.2 µm, respectively, Whatman, UK) with a 1.5 ml Lipex Extruder (Northern Lipids, Canada). Size determination of extruded liposomes was done by light scattering using a Zetasizer 1000HS instrument (Malvern Instruments, UK). For quantification of encapsulated antigen and/or melittin, a fraction of the homogenous liposomes were loaded on a Sephadex G50 Coarse (Amersham Biosciences, Switzerland) gel-filtration column and separated from non-encapsulated peptide. Antigen and/or melittin quantification was done on an Äkta Explorer 10 (Amersham Biosciences, Switzerland) using a CC 125/4.6 Nucleosil 100-5 C8 reverse-phase column (Macherey-Nagel, Switzerland).

Example 5

This example describes a method for the preparation of chimeric proteoliposomes. Viruses: Influenza viruses of the X-31 recombinant strain and the A/PR/8/34 (PR8) strain, propagated in the allantoic cavity of embryonated eggs (Gerhard, J. Exp. Med. 144: 985-995, 1976), were obtained from Berna Biotech (Bern, Switzerland). Chemicals: N-(4,4-difluoro-5,7-diphenyl-4-bora-3a,4a-diaza-s-indacene-3-propionyl)-1,2-dihexadecanoyl-sn-glycero-3-phosphoethanolamine (Bodipy 530/550-DHPE) and Lissamine™ rhodamine B 1,2-dihexadecanoyl-sn-glycero-3-phosphoethanolamine, triethylammonium salt (Rh-DHPE) were from Molecular Probes Europe (Leiden, The Netherlands).

For the preparation of chimeric IRIVs, a solution of 4 mg purified Influenza A/Singapore and X-31 hemagglutinin was centrifuged for 1 hour at 100,000×g and the pellet was dissolved in 1.33 ml of OEG/PBS. 32 mg PC, 6 mg PE and the PE-antigen/adjuvant were dissolved in a total volume of 2.66 ml PBS-OEG. The phospholipids and the hemagglutinin solution were mixed and sonicated for 1 min. This solution was then centrifuged for 1 hour at 100,000×g and the supernatant was sterile filtered (0.22 µm). Virosomes were then formed by detergent removal as indicated in example 2.

Preparation of chimeric proteoliposomes: Chimeric virosomes (600 µl in PBS) were incubated with 200 µl of PC/PG LUVs at 15° C. in PBS under constant stirring. To trigger the fusion the pH was adjusted to about 4.5 with 15 µl of 1 M HCl. After incubation for 30 min, the mixture was neutralized with 15 µl of 1 M NaOH and fusion products were extruded ten times through 0.2 µm polycarbonate membranes as described in example 4. For in vitro fusion measurements by fluorescence resonance energy transfer (FRET), the following assay was developed: 0.75 mol % of Bodipy530/550-DHPE and 0.25 mol % of Rh-DHPE were incorporated into LUVs consisting of PC/PG (70:30). Fluorescence measurements were carried out at distinct temperatures between 4° C. and 42° C. in 5 mM sodium phosphate buffer pH 7.5, 100 mM NaCl, in a final volume of 0.8 ml in 2.5 ml PMMA microcuvettes (VWR, Switzerland) under continous stirring. Typically, 1 µl of labeled liposomes (0.3 µmol phospholipid) were mixed with 5-50 µl of virosomes and fusion was triggered by addition of 3.75-7 µl of 1 M HCl, resulting in a pH around 4.5. The increase in fluorescence was recorded continuously at excitation and emission wavelengths of 530 nm and 550 nm, respectively, with an excitation slit of 2.5 nm and an emission slit of 15.0 nm. Measurements were carried out with a LS 55 Luminescence spectrometer (Perkin Elmer Instruments, USA) equipped with a thermostated cuvette holder and a magnetic stirring device. The maximal fluorescence at infinite probe dilution was reached after addition of Triton X-100 (0.5% (v/v) final conc.).

Example 6

This example shows a method of preparing IRIVs containing antigen/mel/ODN on the surface. IRIVs with antigen and mel on its surface were prepared as outlined in example 2. ODN were added to this IRIVs after detergent removal and incubated for 30 min at RT under shaking to allow binding to the mel peptide.

Example 7

This example shows a method of preparing IRIVs with antigen/mel/ODN encapsulated. The general method for peparing IRIVs with antigen and mel encapsulated is outlined in example 3. To prepare IRIVs with antigen/mel and ODN encapsulated, ODN were added to the peptide mixture in OEG/PBS to allow formation of the mel/ODN complex before the phospholipids, the dissolved virus solution and the peptide/ODN solution were mixed and sonicated for 1 min. Final preparation of IRIVs is as explained in example 3.

An alternative method for preparing IRIVs with antigen/mel/ODN encapsulated is based on example 4. For antigen and melittin-liposomes with hydrophobic antigen, 2-3.5 mg antigen and melittin were dissolved in methanol and added to the phospholipid mixture before solvent removal. The dried lipid film was hydrated with 500 µl PBS containing the ODN. For antigen and melittin-liposomes with hydrophilic antigen, the dried lipid film was hydrated with 350 µl PBS containing 2-3.5 mg peptide, mel and ODN to be encapsulated. Final preparation of LUVs and chimeric IRIVs, respectively, is as explained in example 4.

Example 8

This example shows a method of preparing IRIVs containing antigen/mel/ODN on the surface and antigen/mel/ODN encapsulated in the same IRIV. IRIVs with antigen/mel/ODN encapsulated and antigen/mel/ODN on the surface were prepared by combining the methods as explained in examples 6 and 7. Antigen and mel coupled to PE were prepared as outlined in example 2. Additionally, antigen, mel and ODN were dissolved in OEG/PBS as explained in example 7 (section 1). The phospholipids, the dissolved virus solution, the peptide-coupled phospholipids and the peptide/ODN solution were mixed and sonicated for 1 min. Final preparation of IRIVs is as in example 6.

This section describes an alternative method for preparing IRIVs with antigen/mel/ODN on its surface and antigen/mel/

ODN encapsulated in the same IRIV. Preparation of liposomes (LUVs) with antigen/mel/ODN encapsulated is explained in example 7 (section 2). Preparation of chimeric IRIVs with influenza A/Singapore and X-31 hemagglutinin with antigen/mel on its surface is outlined in example 5. Fusion of liposomes with antigen/mel/ODN encapsulated with chimeric IRIVs with antigen/mel on its surface under conditions outlined in example 5 resulted in IRIV with antigen/mel/ODN encapsulated and antigen/mel on the surface. Final preparation of IRIVs is as in example 5.

Example 9

This example shows a method of preparing IRIVs containing antigen/mel-ODN on the surface, IRIVs with antigen/mel-ODN encapsulated, and IRIVs containing antigen/mel-ODN on the surface and encapsulated in the same IRIV, respectively, where the mel/ODN complex is covalently linked. Peptide-ODN crosslinking was obtained with a standard biochemical technique as for example formaldehyde crosslinking (1% v/v) (Solomon et al., Cell 53:937-947, 1988; Dedon et al. Mol. Cell. Biol. 11:1729-1733, 1991). The Mel-ODN complex was crosslinked and purified separately, and then used as described in examples 6-8.

Example 10

This example shows how the adjuvant effect of the melittin peptide is further potentiated by its combination with IRIVs. Preparation of vaccines: Peptides (OVA257-64: SIINFEKL (SEQ ID NO: 8), Cys-OVA257-64: CSIINFEKL (SEQ ID NO: 9), and Cys-Mel-OVA257-64: CKRKRQKRKRQSIINFEKL, SEQ ID NO: 10) were obtained from Bachem (Bubendorf, Switzerland). The pCI/OVA expression vector was provided by R. Schirmbeck (Ulm, Germany), and ODN-1982 (TCCAGGACTTCTCTCAGGTT, SEQ ID NO: 7) was obtained from Microsynth (Switzerland).

Peptide bearing IRIVs were prepared by first crosslinking the Cys terminus of the peptide to PE via GMBS. Briefly, 10 mg PE was resuspended in 200 μl chloroform/methanol 9:1 and 5 μl ttriethylamine (99%) and 1.7 mg GMBS was added. The mixture was incubated at RT for 1 hour with gentle agitation and then concentrated on a speedvac at RT. The pellet was resuspended in 2 ml OEG/PBS and 6 mg Cys-Mel-OVA was added. After 1 hour incubation at RT it was mixed with 4 mg influenza A/Singapore and 32 mg PC resuspended in 2 ml OEG/PBS. The mixture was sonicated for 1 min and centrifuged for 1 h at 100,000×g at RT. The supernatant was sterile filtered and OEG was removed by four incubations with Biobeads (1 h, 15 min, 30 min, 30 min at RT).

C57Bl/6 mice were injected i.m. with 100 μl PBS containing:

1) 100 μg pCI/OVA
2) 50 μg Cys-OVA257-64
3) 50 μg Cys-OVA257-64+30 μg ODN-1982
4) 50 μg Cys-Mel-OVA257-64
5) 50 μg Cys-Mel-OVA257-64+30 μg ODN-1982
6) IRIV with 50 μg Cys-Mel-OVA257-64 crosslinked to surface
7) IRIV with 50 μg Cys-Mel-OVA257-64 crosslinked to surface+30 μg ODN-1982
8)—PBS buffer only Intracellular IFN-γ staining: 14 days after immunization mice were sacrificed and splenocytes were isolated. After lysis of red blood cells with lysis buffer (8.34 g $NH_4Cl$, 0.037 g EDTA, 1 g $NaHCO_3$ per 1 $H_20$) spleen cells were incubated in RPMI-1640 medium with 0.3% (w/v) BSA, 20 U/ml human recombinant IL-2, 5 μg/ml brefeldin A, and with or without 0.25 μg/ml OVA 257-64 peptide for 5 h at 37° C. Cells were harvested, preincubated with 1 μg/ml anti-mouse CD16/CD32 mAb (Pharmingen) for 10 min at 4° C. and surface stained with FITC-conjugated anti-mouse CD8 mAb (Pharmingen) for 30 min at 4° C. Surface stained cells were fixed and permeabilized with CytoFix/CytoPerm (Pharmingen) according to the manufacturer's protocol. Permeabilized cells were stained with PE-conjugated anti-mouse IFN-γ mAb (Pharmingen) for 30 min at 4° C. Stained cells were resuspended in PBS and analyzed by flow cytometry (FACSCalibur, Becton Dickinson).

Example 11

This example shows the adjuvant effect of melittin when combined with a target antigen coupled to the surface of a virosome Preparation of vaccines: UK39 Malaria mimetics and melittin were purchased from Bachem (Bubendorf, Switzerland).

UK39 IRIV: 4 mg UK39, 4 mg influenza A/Singapore, 32 mg phosphatidylcholine (PC) and 8 mg phosphatidylethanolamine (PE) were resuspended in 4 ml 100 mM OEG in PBS (OEG-PBS), sonicated for 1 min and centrifugated for 1 h at 100'000×g at 20° C. The supernatant was sterile filtered and OEG was removed by four incubations with Biobeads (1 h, 15 min, 30 min, 30 min at RT).

Balb/c mice were immunized with 100 μl PBS containing:

1) UK39 IRIV (20 μg UK39), or
2) UK39 IRIV (20 μg UK39)+10 μg Melittin

UK39 ELISA: ELISA plates were coated over night at 4° C. with 10 μg/ml UK39 in PBS. After washing with PBS 0.05% Tween20 plates were blocked with 5% dry milk in PBS 2 h at 37° C. Mouse sera from day 21 and 35 were initially diluted 1:10 and titrated in serial 1:2 dilutions in PBS 0.05% Tween20 0.5% dry milk. After 2 h incubation at 37° C. plates were washed and incubated with goat □-mouse IgG HRP Ab (BD Bioscience) (1:5000 in PBS 0.05% Tween20 0.5% dry milk) 1 h 37° C. Plates were developed with OPD-substrate (OPD (O-Phenylendiamine tablets, Fluka, Switzerland, 1 tablet in 50 ml citrate buffer+50 μl H2O2) for 30 min. The reaction was stopped with 1 M H2SO4 and plates were read at 492 nm.

This application incorporates by reference the text file INC-001.TXT, created on Jul. 7, 2008, having 4 kilobytes, which contains the Sequence Listing.

What is claimed is:

1. An immunostimulatory composition comprising a synthetic immunostimulatory peptide comprising at least two repeats of SEQ ID NO: 1 and variants thereof.

2. The immunostimulatory composition of claim 1 further comprising at least one oligonucleotide.

3. The immunostimulatory composition of claims 1 or 2 wherein the oligonucleotide is a non-CpG oligonucleotide.

4. The immunostimulatory composition of claims 1 or 2 wherein the at least one oligonucleotide is complexed with the immunostimulatory peptide.

5. The immunostimulatory composition of claim 1 further comprising a target antigen.

6. The immunostimulatory composition of claim 5, further comprising at least one oligonucleotide wherein the at least one oligonucleotide is covalently linked to the immunostimulatory peptide or target antigen.

7. The immunostimulatory composition claim 5, wherein the immunostimulatory peptide and the target antigen are fused.

8. The immunostimulatory composition claim 5, wherein the immunostimulatory peptide and the target antigen are linked by chemical conjugation.

9. The immunostimulatory composition of claim 5, further comprising a delivery vehicle.

10. The immunostimulatory composition of claim 9, wherein the delivery vehicle is selected from the group consisting of liposomes, virus-like particles, and virosomes.

11. The immunostimulatory composition of claim 9, wherein at least one of the immunostimulatory peptide, target antigen and the oligonucleotide is encapsulated in the delivery vehicle.

12. The immunostimulatory composition of claim 9, wherein at least one of the immunostimulatory peptide, the target antigen and the oligonucleotide are linked to the surface of the delivery vehicle.

13. The immunostimulatory composition of claim 1 wherein the immunostimulatory peptide comprises sequence KRKRQKRKRQ (SEQ ID NO: 2).

14. The immunostimulatory composition of claim 13, further comprising at least one oligonucleotide.

15. The immunostimulatory composition of claim 14, further comprising a target antigen.

16. The immunostimulatory composition claim 15, wherein the immunostimulatory peptide and the target antigen are fused.

17. The immunostimulatory composition claim 15, wherein the immunostimulatory peptide and the target antigen are linked by chemical conjugation.

* * * * *

UNITED STATES PATENT AND TRADEMARK OFFICE
CERTIFICATE OF CORRECTION

PATENT NO.        : 7,538,083 B2  
APPLICATION NO. : 10/983169  
DATED             : May 26, 2009  
INVENTOR(S)       : Rinaldo E. Zurbriggen It is certified that error appears in the above-identified patent and that said Letters Patent is hereby corrected as shown below:

In claim 7, at column 23, line 1, delete "composition claim" and replace it with --composition of claim--

In claim 8, at column 23, line 4, delete "composition claim" and replace it with --composition of claim--

In claim 16, at column 24, line 10, delete "composition claim" and replace it with --composition of claim--

In claim 17, at column 24, line 13, delete "composition claim" and replace it with --composition of claim--

Signed and Sealed this

Eighteenth Day of August, 2009

David J. Kappos  
*Director of the United States Patent and Trademark Office*